(12) United States Patent
Tsuneki et al.

(10) Patent No.: US 7,285,221 B2
(45) Date of Patent: Oct. 23, 2007

(54) COMPOSITION FOR PREVENTING OF SLIME AND METHOD FOR PREVENTING SLIME

(75) Inventors: Takao Tsuneki, Ebina (JP); Naohiro Nagai, Toyonaka (JP); Akira Morita, Machida (JP); Takahiko Uchida, Yamato (JP)

(73) Assignee: Kurita Water Industries, Ltd., Tokyo (JP)

( * ) Notice: Subject to any disclaimer, the term of this patent is extended or adjusted under 35 U.S.C. 154(b) by 314 days.

(21) Appl. No.: 10/515,072

(22) PCT Filed: May 21, 2003

(86) PCT No.: PCT/JP03/06366

§ 371 (c)(1),
(2), (4) Date: Nov. 17, 2004

(87) PCT Pub. No.: WO03/096810

PCT Pub. Date: Nov. 27, 2003

(65) Prior Publication Data

US 2006/0054563 A1    Mar. 16, 2006

(30) Foreign Application Priority Data

May 22, 2002    (JP) .............................. 2002-148123

(51) Int. Cl.
*C02F 1/76*    (2006.01)
(52) U.S. Cl. .................... 210/701; 162/161; 210/698; 210/756; 210/764; 252/181; 422/37; 424/661
(58) Field of Classification Search ................. 424/661
See application file for complete search history.

(56) References Cited

U.S. PATENT DOCUMENTS

| 3,170,883 | A | * | 2/1965 | Owen et al. ........... 252/186.36 |
| 3,328,294 | A | | 6/1967 | Self et al. |
| 4,642,194 | A | | 2/1987 | Johnson |
| 4,759,852 | A | * | 7/1988 | Trulear ....................... 210/699 |
| 5,439,611 | A | * | 8/1995 | Sherbondy et al. ......... 252/180 |
| 6,478,972 | B1 | * | 11/2002 | Shim et al. ................. 210/755 |
| 6,743,372 | B1 | * | 6/2004 | Kleinstuck et al. ......... 252/181 |
| 7,087,251 | B2 | * | 8/2006 | Nalepa ....................... 424/703 |

FOREIGN PATENT DOCUMENTS

| JP | 41-15116 | | 8/1941 |
| JP | 7-206609 | A | 8/1995 |
| JP | 2001-170687 | A | 6/2001 |
| JP | 2001-259652 | A | 9/2001 |

* cited by examiner

*Primary Examiner*—Peter A. Hruskoci
(74) *Attorney, Agent, or Firm*—Frishauf, Holtz, Goodman & Chick, P.C.

(57) ABSTRACT

A composition for preventing formation of slime which comprises a chlorine-based oxidizing agent, a sulfamic acid compound, one of an anionic polymer or a phosphonic acid compound and a process for preventing formation of slime which comprises adding the composition to a water system are disclosed. Troubles caused by slime in cooling water systems, heat-storage water systems, water systems in manufacturing processes of paper and pulp, water systems for collecting dusts and scrubber water systems can be effectively prevented with the composition in a small amount.

12 Claims, 1 Drawing Sheet

COMPOSITION FOR PREVENTING OF SLIME AND METHOD FOR PREVENTING SLIME

This application is the U.S. national phase application of International Application PCT/JP03/06366 filed May 21, 2003.

TECHNICAL FIELD

The present invention relates to a composition for preventing formation of slime and a process for preventing formation of slime. More particularly, the present invention relates to a composition for effectively preventing troubles caused by slime in cooling water systems, heat-storage water systems, water systems in manufacturing processes of paper and pulp, water systems for collecting dusts and scrubber water systems in a small amount and a process using the composition.

BACKGROUND ART

Water is highly utilized in cooling water systems, water systems in manufacturing processes of paper and pulp, water systems for collecting dusts and scrubber water systems due to insufficient water resources. For example, the amount of forced blow is decreased in the highly concentrated operation of open circulation cooling water systems. When water is highly utilized as shown in the above example, the quality of water is lowered due to concentration of dissolved salts and nutrients and slime is formed from a mixture containing microorganisms such as bacteria, fungi and algae, sand and dusts. When slime is formed, the heat efficiency in heat exchangers decreases and the flow of water is suppressed. Local corrosion of instruments and pipings takes place at portions covered with the attached slime.

To prevent troubles caused by slime such as those described above, utilization of various antimicrobial agents has been proposed. For example, in Japanese Patent Application Publication No. Showa 41(1966)-15116, as the process for suppressing growth of microorganisms in the flow of treated water, a process which comprises mixing a solution of a salt of hypochlorous acid and a solution of a salt of sulfamic acid to react these compounds and form a solution of a reaction product comprising a salt of N-chlorosulfamic acid, and supplying the formed solution into an aqueous flow for treatment, is disclosed. As higher utilization of cooling water further proceeds, the troubles caused by slime also increase further and it is required that an antimicrobial agent be added in a higher concentration. However, when an oxidative antimicrobial agent is used, it is difficult that the concentration of the added agent is increased since the possibility of corrosion of metals increases. Moreover, since the oxidative antimicrobial agent exhibits poor penetration into slime although the oxidizing ability is great, it is difficult that the troubles caused by slime are suppressed once the troubles take place.

In Japanese Patent Application Laid-Open No. Heisei 7(1995)-206609, taurine chloramine and others are proposed as novel bactericides containing a compound having halogen and nitrogen as the effective component. Since organic bactericides have a small or no oxidizing ability and exhibit strong penetration into slime, it is possible that the troubles caused by slime are suppressed when the troubles take place. However, the spectrum of the effectiveness for the constituting elements of the slime such as bacteria, fungi and algae is different for each selected agent. Moreover, the cost of the agent is far greater than the oxidative antimicrobial agents and the cost of the treatment markedly increases.

Therefore, an agent and a process for preventing formation of slime which are effective for all constituting elements of slime such as bacteria, fungi and algae with a small amount of the agent even under the condition of severe troubles caused by slime and can prevent formation of slime at a low cost, have been desired.

DISCLOSURE OF THE INVENTION

The present invention has an object of providing a composition and a process for effectively preventing troubles caused by slime by using a small amount of the composition in cooling water systems, heat-storage water systems, water systems in manufacturing processes of paper and pulp, water systems for collecting dusts and scrubber water systems.

As the result of intensive studies by the present inventors to overcome the above problem, it was found that a chlorine-based oxidizing agent was kept stable in a composition which comprised the chlorine-based oxidizing agent, a sulfamic acid compound, and one of an anionic polymer or a phosphonic acid compound, and an excellent effect of preventing formation of slime was exhibited to the constituting elements of the slime such as bacteria, fungi and algae. The present invention has been completed based on this knowledge.

The present invention provides:

(1) A composition for preventing formation of slime which comprises a chlorine-based oxidizing agent, a sulfamic acid compound and a compound selected from an anionic polymer and a phosphonic acid compound;

(2) A composition for preventing formation of slime according to (1), wherein the anionic polymer has a weight-average molecular weight in the range of 500 to 50,000;

(3) A composition for preventing formation of slime according to (1), wherein said composition has a pH of 12 or greater, the composition comprizing (a) sodium hypochlorite having a concentration of effective chlorine of 1 to 8% by weight, (b) 1.5 to 9% by weight of sulfamic acid, (c) 2.5 to 20% by weight of sodium hydroxide and (d) at least one of the anionic polymer, the solid concentration of which is 0.5 to 4% by weight or at least one of the phosphonic acid compound, the solid concentration of which is 0.5 to 4% by weight; each of the concentrations expressed in percentage being calculated based on the total amount by weight of the composition;

(4) A composition for preventing formation of slime according to (1), wherein said composition comprises:

component A, which comprises the chlorine-based oxidizing agent and has a pH of 12 or greater, said component A comprising (a) sodium hypochlorite having a concentration of effective chlorine of 1 to 8% by weight, (b) 1.5 to 9% by weight of sulfamic acid, (c) 2.5 to 20% by weight of sodium hydroxide, each of aforesaid concentrations expressed in percentage being calculated based on the total amount by weight of component A; and component B, which comprises (d) at least one of the anionic polymer, the solid concentration of which is 10 to 60% by weight or at least one of the phosphonic acid compound, the solid concentration of which is 10 to 60% by weight, each of afore-said concentrations expressed in percentage being calculated based on the total amount by weight of component B;

(5) A composition for preventing formation of slime according to (3), wherein the anionic polymer has a weight-average molecular weight in the range of 500 to 50,000 and said anionic polymer is at least one compound selected from the group consisting of polymaleic acid, polyacrylic acid, a copolymer of acrylic acid and 2-hydroxy-3-allyloxypropane sulfonic acid, a copolymer of acrylic acid and 2-acrylamide-2-methylpropane sulfonic-acid, a copolymer of acrylic acid and isoprene sulfonic acid, a copolymer of acrylic acid and 2-hydroxyethyl methacrylate, a copolymer of acrylic acid, 2-hydroxyethyl methacrylate and isopropylene sulfonic acid, a copolymer of maleic acid and pentene, a copolymer of maleic acid and isobutylene, alkalin metal salts of afore-said anionic polymers and an alkaline earth metal salts of afore-said anionic polymers;

(6) A composition for preventing formation of slime according to (1), wherein the chlorine-based oxidizing agent is at least one compound selected from the group consisting of chlorine, alkali metal hypochlorites, alkali metal chlorites and alkali metal chlorates;

(7) A composition for preventing formation of slime according to (1), wherein the sulfamic compound is at least one compound selected from the group consisting of sulfamic acid, N-methylsulfamic acid, N,N-dimethylsulfamic acid, N-phenylsulfamic acid, alkali metal salts of afore-said sulfamic acids, alkaline earth metal salts of afore-said sulfamic acids and ammonium salts of afore-said sulfamic acids,;

(8) A composition for preventing formation of slime according to (1), wherein the phosphonic acid compound is at least one compound selected from the group consisting of 1-hydroxyethylidene-1,1,-diphosphonic acid, 2-phosphonobutane-1,2,4-tricarboxylic acid, hydroxyphosphonoacetic acid, nitrilotrimethylene-phosphonic acid, ethylenediamine-N,N,N',N'-tetramethylene-phosphonic acid, alkali metal salts of afore-said phosphonic acids, and alkaline metal salts of afore-said phosphonic acids;

(9) A process for preventing formation of slime in a water system, the process comprising adding a composition for preventing formation of slime which comprises a chlorine-based oxidizing agent, a sulfamic acid compound and a compound selected from an anionic polymer and a phosphonic acid compound to said water system;

(10) A process for preventing formation of slime according to (9), wherein the composition for preventing formation of slime has a pH of 12 or greater and comprises (a) sodium hypochlorite having a concentration of effective chlorine of 1 to 8% by weight, (b) 1.5 to 9% by weight of sulfamic acid, (c) 2.5 to 20% by weight of sodium hydroxide and (d) at least one of the anionic polymer, the solid concentration of which is 0.5 to 4% by weight or at least one of the phosphonic acid compound, the solid concentration of which is 0.5 to 4% by weight; each of the concentrations expressed in percentage being calculated based on the total amount by weight of said composition;

(11) A process for preventing formation of slime according to (9), wherein the composition for preventing formation of slime comprises:

component A, which comprises the chlorine-based oxidizing agent and has a pH of 12 or greater, said component A comprising (a) sodium hypochlorite having a concentration of effective chlorine of 1 to 8% by weight, (b) 1.5 to 9% by weight of sulfamic acid, (c) 2.5 to 20% by weight of sodium hydroxide, each of afore-said concentrations expressed in percentage being calculated based on the total amount by weight of component A; and component B, which comprises (d) at least one of the anionic polymer, the solid concentration of which is 10 to 60% by weight or at least one of the phosphonic acid compound, the solid concentration of which is 10 to 60% by weight, each of afore-said concentrations expressed in percentage being calculated based on the total amount by weight of component B; and

(12) A process for preventing formation of slime according to (9), wherein the water system is any one of cooling water system, heat-storage water system, water system in manufacturing processes of paper and pulp, water system for collecting dusts or scrubber water systems.

Figure 1:
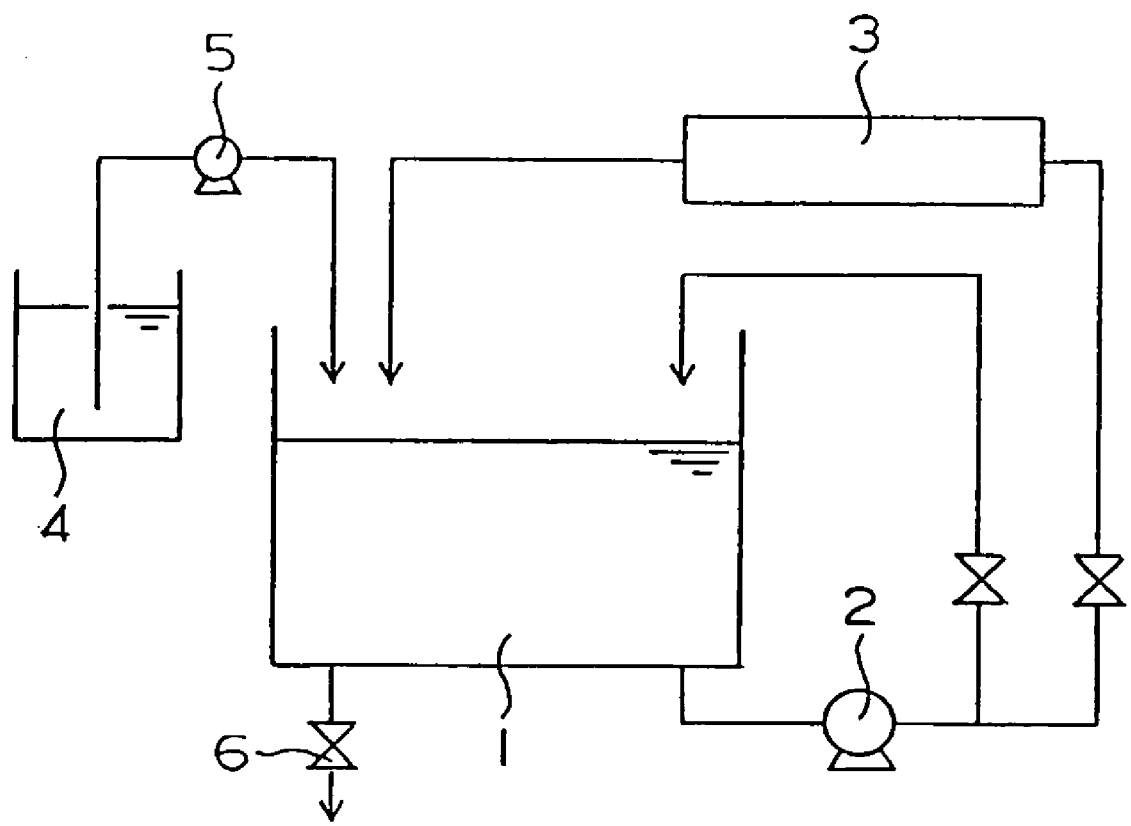
FIG. 1 shows a diagram exhibiting the apparatus used in Examples and Comparative Examples.

The numbers in FIG. 1 has the following meanings.
1: A water tank
2: A circulation pump
3: A column
4: A tank for storing an agent
5: A pump for an agent
6: A valve

THE MOST PREFERRED EMBODIMENT TO CARRY OUT THE INVENTION

The composition for preventing formation of slime comprises a chlorine-based oxidizing agent, a sulfamic acid compound and a compound selected from an anionic polymer and a phosphonic acid compound. The process for preventing formation of slime comprises adding a chlorine-based oxidizing agent, a sulfamic acid compound and a compound selected from an anionic polymer and a phosphonic acid compound to a water system.

Examples of the chlorine-based oxidizing agent used in the present invention include chlorine; alkali metal hypochlorites such as sodium hypochlorite, potassium hypochlorite, alkaline earth metal hypochlorites such as calcium hypochlorite and barium hypochlorite; alkali metal chlorites such as sodium chlorite, potassium chlorite, alkaline earth metal chlorites such as barium chlorite and other metal chlorites such as nickel chlorite; and chlorates such as ammonium chlorate, alkali metal chlorates such as sodium chlorate potassium chlorate, and alkaline earth metal chlorates such as calcium chlorate and barium chlorate. The chlorine-based oxidizing agent may be used singly or in combination of two or more. Among the above agents, hypochlorites are preferable due to easiness in handling.

The sulfamic acid compound used in the present invention is a compound represented by the following general formula [1]:

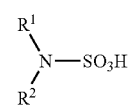

or the salt thereof.

In general formula [1], $R^1$ and $R^2$ represent hydrogen atom or a hydrocarbon group having 1 to 8 carbon atoms. Examples of the sulfamic acid compound represented by the general formula [1] include sulfamic acid in which $R^1$ and $R^2$ in the formula both represent hydrogen atom, N-methylsulfamic acid, N,N-dimethylsulfamic acid and N-phenylsulfamic acid. Examples of the salt of sulfamic acid compound used in the present invention include the alkali metal salt such as the sodium salt and the potassium salt, akaline earth metal salt such as the calcium salt, the strontium salt, the barium salt and the manganese salt, and other metal salts such as the copper salt, the zinc salt, the iron salt, the cobalt salt, the nickel salt, the ammonium salt and the guanidine salt.

It is preferable that the anionic polymer used in the present invention has a weight-average molecular weight in the range of 500 to 50,000, more preferably in the range of 1,000 to 30,000 and most preferably in the range of 1,500 to 20,000.

Examples of the monomer providing the anionic polymer used in the present invention include unsaturated carboxylic acids such as acrylic acid, methacrylic acid and maleic acid; salts of the unsaturated carboxylic acids such as alkali metal salts including the sodium salt and the potassium salt or the alkaline earth metal salts including the calcium salt and magnesium salt; and anhydrides of unsaturated carboxylic acids such as maleic anhydride. These monomers may be used for homopolymerization, copolymerization of two or more or copolymerization of one or more with one or more other copolymerizable monomers. Examples of the other copolymerizable monomer include unsaturated alcohols, esters of unsaturated carboxylic acids, alkenes and monomers having sulfonic acid group. Examples of the unsaturated alcohol include allyl alcohol and methallyl alcohol. Examples of the ester of an unsaturated carboxylic acid include methyl acrylate, ethyl acrylate, hydroxyethyl acrylate and hydroxyethyl methacrylate. Examples of the alkene include isobutylene, n-butylene, diisobutylene and pentene. Examples of the monomer having suit onic acid group include vinylsulfonic acid, 2-hydroxy-3-allyloxy-1-propanesulfonic acid, isoprenesulfonic acid and styrenesulfonic acid. Examples of the anionic polymer used in the present invention include polymaleic acid, polyacrylic acid, a copolymer of acrylic acid and 2-hydroxy-3-allyioxypropane sulfonic acid, a copolymer of acrylic acid and 2-acrylamide-2-methylpropane suilfonic acid, a copolymer of acrylic acid and isoprene sulfonic acid, a copolymer of acrylic acid and 2-hydroxyethyl methacrylate, a copolymer of acrylic acid, 2-hydroxyethyl methacrylate and isopropylene sulfonic acid, a copolymer of maleic acid and pentene, a copolymer of maleic acid and isobutylene, alkalin metal salts of afore-said anionic polymers and an alkaline earth metal salts of afore-said anionic polymers. The concentration of the anionic polymer in the water is 1 mg/L or more preferably 3 mg/L or more as solid content. Examples of the phosphonic acid compound used in the present invention include 1-hydroxyethylidene-1,1-diphosphonic acid, 2-phosphonobutane-1,2,4-tricarboxylic acid; hydroxyphosphonoacetic acid, nitrilotrimethylene-phosphonic acid and ethylenediamineN,N,N',N'-tetramethylene-phosphonic acid or the salts of afore-said acids. Examples of the salt of the phosphonic acid include alkali metal salts such as the lithium salt, the sodium salt and the potassium salt; and alkaline earth metal salts such as the magnesium salt and the calcium salt. The salt of the phosphonic acid may be an ortho-salt in which hydrogen atoms as the characteristic components of the acid are completely substituted or an acidic salt in which some of the hydrogen atoms as the components of the acid remain. The phosphonic acid and the salt of the phosphonic acid may be used singly or in combination of two or more. The concentration of phosphonic acid compound in the water is 1 mg/L or more preferably 3 mg/L as solid content.

The form of the composition for preventing formation of slime is not particularly limited and may be, for example, a one-part agent comprising all of the chlorine-based oxidizing agent, one of the sulfamic acid compounds and a compound selected from one of the anionic polymer and one of the phosphonic acid compounds; or a two-part agent composed of two comprising the components. Examples of the two-part agent include an agent which comprises A-part comprising the chlorine-based oxidizing agent and the sulfamic acid compound and B-part comprising the anionic polymer or the phosphonic acid compound.

When the agent is a one-part agent, it is preferable that pH is adjusted at 12 or greater and more preferably at 13 or greater by adding an alkali such as sodium hydroxide and potassium hydroxide so that stability of the chlorine-based oxidizing agent is maintained. When the agent is a two-part agent, it is preferable that pH of the part comprising the chlorine-based oxidizing agent is adjusted at 12 or greater and more preferably at 13 or greater due to the same reason.

In an embodiment of the one-part agent of the composition for preventing formation of slime, the composition has a pH of 12 or more and comprizes (a) sodium hypochlorite having a concentration of effective chlorine of 1 to 8% by weight preferably 3 to 6% by weight, (b) 1.5 to 9% by weight preferably 4.5 to 7% by weight of sulfamic acid, (c) 2.5 to 20% by weight preferably 7.5 to 15% by weight of sodium hydroxide and (d) at least one of the anionic polymer, the solid concentration of which is 0.5 to 4% by weight preferably 1.5 to 3% by weight or at least one of the phosphonic acid compound, the solid concentration of which is 0.5 to 4% by weight preferably 1.5 to 3% by weight; each of the concentrations expressed in percentage being calculated based on the total amount by weight of the composition. In an embodiment of the two-part agent of the composition for preventing formation of slime, the composition comprises component A, which comprises the chlorine-based oxidizing agent and has a pH of 12 or greater, said component A comprising (a) sodium hypochlorite having a concentration of effective chlorine of 1 to 8% by weight preferably 3 to 6% by weight, (b) 1.5 to 9% by weight preferably 4.5 to 9% by weight of sulfamic acid, (c) 2.5 to 20% by weight preferably 7.5 to 15% by weight of sodium hydroxide, each of afore-said concentrations expressed in percentage being calculated based on the total amount by weight of component A; and component B, which comprises (d) at least one of the anionic polymer, the solid concentration of which is 10 to 60% by weight or at least one of the phosphonic acid compound, the solid concentration of which is 10 to 60% by weight, each of afore-said concentrations expressed in percentage being calculated based on the total amount by weight of component B.

When the composition and the process for preventing formation of slime of the present invention are used, the excellent effects of preventing attachment of slime and preventing accumulation of sludge can be exhibited even when the composition is used in a small amount such that the antimicrobial effect is not obtained. When pasteurization or disinfection is the object of the treatment as in the conventional process, an agent must be added in a great concentration. Slime is dirt containing a mixture of flocks of microorganisms and inorganic substances such as sand and dust attached to pipings and heat transfer pipes of heat exchangers. Sludge is dirt containing a mixture of flocks of microorganisms and inorganic substances such as sand and dusts accumulated at the bottom of water tanks and separating plates of heat exchangers. The attachment of slime and the accumulation of sludge are considered to take place as follows. Growth and aggregation of inorganic particles such as scales, sands, dusts and products of corrosion and growth and aggregation of microorganisms proceed simultaneously and the size of minute floating substances gradually increases. Inorganic particles are occluded into viscous substances formed by microorganisms, i.e., the so-called bioflocculation takes place, and the attachment of slime and the accumulation of sludge take place. When the composition and the process for preventing formation of slime of the present invention are used, it is considered that a synergistic effect is exhibited by the components for suppressing the bioflocculation and the components exhibiting the effects of dispersing inorganic substances and sealing inorganic substance by the chelating effect, and the attachment of slime and the accumulation of sludge can be effectively prevented. The composition and the process for preventing formation of slime of the present invention can be used advantageously in cooling water systems, water systems in manufacturing processes of paper and pulp, water systems for collecting dusts and scrubber water systems.

EXAMPLES

The present invention will be described more specifically with reference to examples in the following. However, the present invention is not limited to the examples.

FIG. 1 shows a diagram exhibiting the apparatus used in Examples and Comparative Examples. From a water tank 1 holding 15 liters of water, test water was passed at a rate of 10 liters/minute through a column 3 and returned to the water tank 1 using a circulating pump 2. In the column 3, a test board made of a synthetic rubber and having a surface area of 40 cm$^2$ was disposed to a supporting pole to measure the amount of attachment of slime.

In a water tank 4, test liquid for supplement prepared in advance was stored and transferred into the water tank 1 at a rate of 5 ml/minute using a pump for an agent 5. The test liquid for supplement was prepared by adding calcium chloride and sodium hydrogencarbonate to city water, which was dechlorinated by passing through a column of active carbon, in amounts such that the calcium hardness was 150 mg CaCO$_3$/liter and the acid consumption (pH 4.8) was 150 mg CaCO$_3$/liter. As the nutrient for microorganisms, 100 mg/liter of citric acid was added. To the obtained solution, a test agent was added and pH was adjusted at 8.5 by adding sodium hydroxide.

When the test was started, dirt was added into the water in the water tank 1 in an amount such that the turbidity of the water was 50. As the dirt, a concentrated liquid of reverse washing discharged from filters for industrial water in Chiba area was used. The dirt was added into the water tank 1 in an amount corresponding to a turbidity of 25 at each time when 48 hours and 96 hours had passed after the start of the test.

The number of microorganisms in the circulating water and the turbidity of the circulating water were measured 48 hours, 72 hours and 120 hours after the start of the test. The test board of synthetic rubber attached to the column 3 was taken out 120 hours after the start of the test. After slime attached to the test board was cleaved and dried to the constant weight at 105° C., the weight of the slime was measured and the amount of the attached slime was obtained.

A valve 6 at a lower portion of the water tank 1 was opened and the water in the water tank 1 was removed 120 hours after the start of the test. The valve 6 was then closed again. Into the water tank 1, 200 ml of pure water was added and dirt accumulated at the lower portion of the water tank was suspended using a brush. The valve was opened and the formed suspension was taken out. After the dirt was separated using a centrifuge and dried to the constant weight at 105° C., the weight of the dirt was measured and the amount of accumulated sludge was obtained.

As part A of the test agent, a mixed liquid composed of 40% by weight of an aqueous solution of sodium hypochlorite having a concentration of effective chlorine of 12% by weight, 8% by weight of a sulfamic acid, 10% by weight of sodium hydroxide and 42% by weight of water was used. This mixed liquid is a solution conventionally used as the agent for preventing formation of slime. As part B of the agent, an anionic polymer or a phosphonic acid was used.

Comparative Example 1

In place of the test liquid for supplement, water for supplement prepared as follows was used. To city water dechlorinated by passing through a layer of active carbon, calcium chloride and calcium hydrogencarbonate were added in an amount such that the calcium hardness was 150 mg CaCO$_3$/liter and the acid consumption (pH 4.8) was 150 mg CaCO$_3$/liter; 100 mg/liter of citric acid was added as the nutrient for microorganisms; and pH of the prepared water was adjusted at 8.5 by adding sodium hydroxide. The test was conducted for 120 hours.

The number of microorganisms in the circulating water was $1.7 \times 10^5$ after 48 hours, $1.2 \times 10^5$ after 72 hours and $1.3 \times 10^5$ after 120 hours. The turbidity of the circulating water was 3.5 after 48 hours, 2.1 after 72 hours and 2.8 after 120 hours. The amount of attached slime was 20.0 mg/dm$^2$ and the amount of accumulated sludge was 94.4 mg after 120 hours.

Example 1

To the test liquid for supplement, part A of the test agent in an amount such that the concentration of effective chlorine was 5 mg/liter and polymaleic acid [manufactured by GREAT LAKES CHEMICAL Company; BELCLENE; the weight-average-molecular weight: 2,730] in an amount such that the concentration of solid components was 5 mg/liter as part B of the test agent were added and the test was conducted for 120 hours.

The number of microorganisms in the circulating water was $2.8 \times 10^6$ after 48 hours, $2.4 \times 10^7$ after 72 hours and $3.2 \times 10^7$ after 120 hours. The turbidity of the circulating water was 9.5 after 48 hours, 10.2 after 72 hours and 12.2 after 120 hours. The amount of attached slime was 1.0 mg/dm$^2$, the fraction of preventing attachment of slime was 95.0%, the amount of accumulated sludge was 5.2 mg and the fraction of preventing accumulation of sludge was 94.5% after 120 hours.

Example 2

The test was conducted in accordance with the same procedures as those conducted in Example 1 except that a maleic acid-isobutylene copolymer [manufactured by KURARAY Co., Ltd.; ISOBAN; the weight-average molecular weight: 10,800] was used as component B in place of polymaleic acid.

Example 3

The test was conducted in accordance with the same procedures as those conducted in Example 1 except that an acrylic acid-hydroxyallyloxypropanesulfonic acid copolymer [manufactured by NIPPON SHOKUBAI Co., Ltd.; AQUARICK GL; the weight-average molecular weight: 10,700] was used as component B in place of polymaleic acid.

Example 4

The test was conducted in accordance with the same procedures as those conducted in Example 1 except that 1-hydroxyethylidene-1,1-diphosphonic acid [manufactured by MONSANTO Company; DEQUEST 2010] was used as component B in place of polymaleic acid.

Example 5

The test was conducted in accordance with the same procedures as those conducted in Example 1 except that 2-phosphonobutane-1,2,4-tricarboxylic acid [manufactured by BAYER Company; BAYHIBIT AM] was used as component B in place of polymaleic acid.

Example 6

The test was conducted in accordance with the same procedures as those conducted in Example 1 except that hydroxyphosphonoacetic acid [manufactured by GREAT LAKES Company; BELCORE 575] was used as component B in place of polymaleic acid.

Comparative Example 2

The test was conducted in accordance with the same procedures as those conducted in Example 1 except that part A of the test agent alone was added to the test liquid for supplement in an amount such that the concentration of effective chlorine was 5 mg/liter.

The number of microorganisms in the circulating water was $1.4 \times 10^5$ after 48 hours, $2.2 \times 10^6$ after 72 hours and $2.8 \times 10^6$ after 120 hours. The turbidity of the circulating water was 5.7 after 48 hours, 5.4 after 72 hours and 5.7 after 120 hours. The amount of attached slime was 8.7 mg/dm$^2$, the fraction of preventing attachment of slime was 56.5%, the amount of accumulated sludge was 35.5 mg and the fraction of preventing accumulation of sludge was 62.4% after 120 hours.

Comparative Example 3

The test was conducted in accordance with the same procedures as those conducted in Comparative Example 2 except that part A was added in an amount such that the concentration of effective chlorine was 10 mg/liter.

Comparative Example 4

The test was conducted in accordance with the same procedures as those conducted in Example 1 except that a maleic acid-isobutylene copolymer [manufactured by KURARAY Co., Ltd.; ISOBAN] alone was added to the test liquid for supplement as part B of the test agent in an amount such that the concentration of solid components was 5 mg/liter.

Comparative Example 5

The test was conducted in accordance with the same procedures as those conducted in Comparative Example 4 except that a maleic acid-isobutylene copolymer [manufactured by KURARAY Co., Ltd.; ISOBAN] was added in an amount such that the concentration of solid components was 10 mg/liter.

Comparative Example 6

The test was conducted in accordance with the same procedures as those conducted in Example 1 except that an acrylic acid-hydroxyallyloxy-propanesulfonic acid copolymer [manufactured by NIPPON SHOKUBAI Co., Ltd.; AQUARICK GL] alone was added to the test liquid for supplement as part B of the test agent in an amount such that the concentration of solid components was 5 mg/liter.

Comparative Example 7

The test was conducted in accordance with the same procedures as those conducted in Comparative Example 6 except that the acrylic acid-hydroxyallyloxypropanesulfonic acid copolymer [manufactured by NIPPON SHOKUBAI Co., Ltd.; AQUARICK GL] was added in an amount such that the concentration of solid components was 10 mg/liter.

Comparative Example 8

The test was conducted in accordance with the same procedures as those conducted in Example 1 except that 1-hydroxyethylidene-1,1-diphosphonic acid [manufactured by MONSANTO Company; DEQUEST 2010] alone was added to the test liquid for supplement as part B of the test agent in an amount such that the concentration of solid components was 5 mg/liter.

Comparative Example 9

The test was conducted in accordance with the same procedures as those conducted in Comparative Example 8 except that 1-hydroxyethylidene-1,1-diphosphonic acid [manufactured by MONSANTO Company; DEQUEST 2010] was added in an amount such that the concentration of solid components was 10 mg/liter.

Comparative Example 10

The test was conducted in accordance with the same procedures as those conducted in Example 1 except that 2-phosphonobutane-1,2,4-tricarboxylic acid [manufactured by BAYER Company; BAYHIBIT AM] alone was added to the test liquid for supplement as part B of the test agent in an amount such that the concentration of solid components was 5 mg/liter.

Comparative Example 11

The test was conducted in accordance with the same procedures as those conducted in Comparative Example 10 except that 2-phosphonobutane-1,2,4-tricarboxylic acid [manufactured by BAYER Company; BAYHIBIT AM] was added in an amount such that the concentration of solid components was 10 mg/liter.

Comparative Example 12

The test was conducted in accordance with the same procedures as those conducted in Example 1 except that hydroxyphosphonoacetic acid [manufactured by GREAT LAKES Company; BELCORE 575] alone was added to the test liquid for supplement as part B of the test agent in an amount such that the concentration of solid components was 5 mg/liter.

Comparative Example 13

The test was conducted in accordance with the same procedures as those conducted in Comparative Example 12 except that hydroxy-phosphonoacetic acid [manufactured by GREAT LAKES Company; BELCORE 575] was added in an amount such that the concentration of solid components was 10 mg/liter.

The results of the measurements of the attachment of slime and the accumulation of sludge in Examples 1 to 6 and Comparative Examples 1 to 13 are shown in Table 1. The numbers of microorganisms in the circulating water are shown in Table 2 and the turbidities of the circulating water are shown in Table 3.

TABLE 1

| | Part A (effective chlorine) (mg/liter) | Part B type | Part B concn. of solid components (mg/liter) | Attachment of slime amount (mg/dm$^2$) | Attachment of slime fraction of prevention (%) | Accumulation of sludge amount (mg) | Accumulation of sludge fraction of prevention (%) |
|---|---|---|---|---|---|---|---|
| Comparative Example 1 | — | — | — | 20.0 | — | 94.4 | — |
| Example 1 | 5 | polymaleic acid | 5 | 1.0 | 95.0 | 5.2 | 94.5 |
| Example 2 | 5 | maleic acid-isobutylene copolymer | 5 | 1.6 | 92.0 | 6.5 | 93.1 |
| Example 3 | 5 | acrylic acid-hydroxy-allyloxypropanesulfonic acid copolymer | 5 | 1.8 | 91.0 | 7.2 | 92.4 |
| Example 4 | 5 | 1-hydroxyethylidene-1,1-diphosphonic acid | 5 | 1.7 | 91.5 | 5.5 | 94.2 |
| Example 5 | 5 | 2-phosphonobutane-1,2,4-tricarboxylic acid | 5 | 2.0 | 90.0 | 6.8 | 92.8 |
| Example 6 | 5 | hydroxyphosphono-acetic acid | 5 | 1.9 | 90.5 | 7.6 | 92.0 |
| Comparative Example 2 | 5 | — | — | 8.7 | 56.5 | 35.5 | 62.4 |
| Comparative Example 3 | 10 | — | — | 4.2 | 79.0 | 18.2 | 80.7 |
| Comparative Example 4 | — | maleic acid-isobutylene copolymer | 5 | 19.0 | 5.0 | 60.3 | 36.1 |
| Comparative Example 5 | — | maleic acid-isobutylene copolymer | 10 | 16.5 | 17.5 | 48.7 | 48.4 |
| Comparative Example 6 | — | acrylic acid-hydroxy-allyloxypropanesulfonic acid copolymer | 5 | 18.4 | 8.0 | 65.5 | 30.5 |
| Comparative Example 7 | — | acrylic acid-hydroxy-allyloxypropanesulfonic acid copolymer | 10 | 17.7 | 11.5 | 40.3 | 57.3 |
| Comparative Example 8 | — | 1-hydroxyethylidene-1,1-diphosphonic acid | 5 | 17.3 | 13.5 | 42.8 | 54.7 |
| Comparative Example 9 | — | 1-hydroxyethylidene-1,1-diphosphonic acid | 10 | 16.1 | 19.5 | 39.6 | 58.1 |
| Comparative Example 10 | — | 2-phosphonobutane-1,2,4-tricarboxylic acid | 5 | 19.2 | 4.0 | 55.5 | 41.2 |
| Comparative Example 11 | — | 2-phosphonobutane-1,2,4-tricarboxylic acid | 10 | 16.5 | 17.5 | 48.8 | 48.3 |
| Comparative Example 12 | — | hydroxyphosphono-acetic acid | 5 | 18.7 | 6.5 | 57.6 | 39.0 |
| Comparative Example 13 | — | hydroxyphosphono-acetic acid | 10 | 16.5 | 4.0 | 51.1 | 45.9 |

TABLE 2

| | Part A (effective chlorine) (mg/liter) | Part B type | Part B concn. of solid components (mg/liter) | Number of microorganisms in circulating water (/ml) | | |
|---|---|---|---|---|---|---|
| | | | | after 48 hours | after 72 hours | after 120 hours |
| Comparative Example 1 | — | — | — | $1.7 \times 10^5$ | $1.2 \times 10^5$ | $1.3 \times 10^5$ |
| Example 1 | 5 | polymaleic acid | 5 | $2.8 \times 10^6$ | $2.4 \times 10^7$ | $3.2 \times 10^7$ |
| Example 2 | 5 | maleic acid-isobutylene copolymer | 5 | $7.5 \times 10^5$ | $4.2 \times 10^6$ | $4.8 \times 10^6$ |
| Example 3 | 5 | acrylic acid-hydroxy-allyloxypropanesulfonic acid copolymer | 5 | $3.7 \times 10^6$ | $4.8 \times 10^6$ | $6.2 \times 10^6$ |
| Example 4 | 5 | 1-hydroxyethylidene-1,1-diphosphonic acid | 5 | $3.3 \times 10^6$ | $3.2 \times 10^6$ | $4.2 \times 10^6$ |
| Example 5 | 5 | 2-phosphonobutane-1,2,4-tricarboxylic acid | 5 | $4.3 \times 10^6$ | $2.9 \times 10^6$ | $3.2 \times 10^6$ |
| Example 6 | 5 | hydroxyphosphonoacetic acid | 5 | $4.7 \times 10^6$ | $2.6 \times 10^6$ | $2.8 \times 10^6$ |
| Comparative Example 2 | 5 | — | — | $1.4 \times 10^5$ | $2.2 \times 10^6$ | $2.8 \times 10^6$ |
| Comparative Example 3 | 10 | — | — | $4.3 \times 10^5$ | $7.4 \times 10^6$ | $7.2 \times 10^6$ |
| Comparative Example 4 | — | maleic acid-isobutylene copolymer | 5 | $2.9 \times 10^5$ | $3.5 \times 10^5$ | $3.8 \times 10^5$ |
| Comparative Example 5 | — | maleic acid-isobutylene copolymer | 10 | $3.4 \times 10^5$ | $3.9 \times 10^5$ | $7.2 \times 10^5$ |
| Comparative Example 6 | — | acrylic acid-hydroxy-allyloxypropanesulfonic acid copolymer | 5 | $7.2 \times 10^5$ | $3.6 \times 10^5$ | $4.2 \times 10^5$ |
| Comparative Example 7 | — | acrylic acid-hydroxy-allyloxypropanesulfonic acid copolymer | 10 | $6.6 \times 10^5$ | $4.6 \times 10^5$ | $3.8 \times 10^5$ |
| Comparative Example 8 | — | 1-hydroxyethylidene-1,1-diphosphonic acid | 5 | $7.2 \times 10^5$ | $5.5 \times 10^5$ | $4.9 \times 10^5$ |
| Comparative Example 9 | — | 1-hydroxyethylidene-1,1-diphosphonic acid | 10 | $1.3 \times 10^6$ | $4.9 \times 10^5$ | $6.8 \times 10^5$ |
| Comparative Example 10 | — | 2-phosphonobutane-1,2,4-tricarboxylic acid | 5 | $6.7 \times 10^5$ | $8.4 \times 10^5$ | $4.2 \times 10^5$ |
| Comparative Example 11 | — | 2-phosphonobutane-1,2,4-tricarboxylic acid | 10 | $3.8 \times 10^6$ | $8.9 \times 10^5$ | $7.6 \times 10^5$ |
| Comparative Example 12 | — | hydroxyphosphonoacetic acid | 5 | $4.8 \times 10^5$ | $5.5 \times 10^5$ | $7.2 \times 10^5$ |
| Comparative Example 13 | — | hydroxyphosphonoacetic acid | 10 | $6.6 \times 10^5$ | $3.5 \times 10^5$ | $4.9 \times 10^5$ |

TABLE 3

| | Part A (effective chlorine) (mg/liter) | Part B type | Part B concn. of solid components (mg/liter) | Turbidity of circulating water (degree) | | |
|---|---|---|---|---|---|---|
| | | | | after 48 hours | after 72 hours | after 120 hours |
| Comparative Example 1 | — | — | — | 3.5 | 2.1 | 2.8 |
| Example 1 | 5 | polymaleic acid | 5 | 9.5 | 10.2 | 12.2 |
| Example 2 | 5 | maleic acid-isobutylene copolymer | 5 | 8.6 | 7.7 | 15.2 |
| Example 3 | 5 | acrylic acid-hydroxy-allyloxypropanesulfonic acid copolymer | 5 | 8.8 | 11.2 | 14.4 |
| Example 4 | 5 | 1-hydroxyethylidene-1,1-diphosphonic acid | 5 | 9.1 | 9.3 | 11.8 |

TABLE 3-continued

|  | Part A (effective chlorine) (mg/liter) | Part B type | concn. of solid components (mg/liter) | Turbidity of circulating water (degree) | | |
|---|---|---|---|---|---|---|
|  |  |  |  | after 48 hours | after 72 hours | after 120 hours |
| Example 5 | 5 | 2-phosphonobutane-1,2,4-tricarboxylic acid | 5 | 8.3 | 9.5 | 14.3 |
| Example 6 | 5 | hydroxyphosphono-acetic acid | 5 | 8.0 | 8.5 | 10.9 |
| Comparative Example 2 | 5 | — | — | 5.7 | 5.4 | 5.7 |
| Comparative Example 3 | 10 | — | — | 5.5 | 5.7 | 9.7 |
| Comparative Example 4 | — | maleic acid-isobutylene copolymer | 5 | 3.9 | 3.6 | 3.9 |
| Comparative Example 5 | — | maleic acid-isobutylene copolymer | 10 | 4.2 | 4.5 | 3.6 |
| Comparative Example 6 | — | acrylic acid-hydroxy-allyloxypropanesulfonic acid copolymer | 5 | 3.8 | 3.5 | 4.2 |
| Comparative Example 7 | — | acrylic acid-hydroxy-allyloxypropanesulfonic acid copolymer | 10 | 4.1 | 4.1 | 3.8 |
| Comparative Example 8 | — | 1-hydroxyethylidene-1,1-diphosphonic acid | 5 | 3.7 | 3.6 | 3.9 |
| Comparative Example 9 | — | 1-hydroxyethylidene-1,1-diphosphonic acid | 10 | 3.7 | 3.9 | 4.5 |
| Comparative Example 10 | — | 2-phosphonobutane-1,2,4-tricarboxylic acid | 5 | 3.9 | 4.1 | 4.6 |
| Comparative Example 11 | — | 2-phosphonobutane-1,2,4-tricarboxylic acid | 10 | 4.3 | 3.8 | 4.2 |
| Comparative Example 12 | — | hydroxyphosphono-acetic acid | 5 | 4.1 | 4.5 | 4.1 |
| Comparative Example 13 | — | hydroxyphosphono-acetic acid | 10 | 4.3 | 4.7 | 4.5 |

As shown in Table 1, when the results in Examples 1 to 6, in which part A comprising sodium hypochlorite and sulfamic acid in amounts such that the concentration of effective chlorine was 5 mg/liter and part B comprising the anionic polymer or the phosphonic acid in an amount such that the concentration of solid components was 5 mg/liter were used in combination, were compared with the results in Comparative Example 1 in which no agent for preventing formation of slime was added, in Examples 1 to 6, the amount of attachment of slime and the amount of accumulation of sludge were both smaller than on tenth of those in Comparative Examples and the fraction of preventing attachment of slime and the fraction of preventing accumulation of sludge both exceeded 90%. As shown in Table 2, in Examples 1 to 6, the effect of preventing attachment of slime and the effect of preventing accumulation of sludge were exhibited even when the number of microorganisms in the circulating water was relatively great and the concentration of the agent for preventing formation of slime was not in the range exhibiting the microbicidal effect. As shown in Table 3, in Examples 1 to 6, the flocculation of suspended substances did not take place and the attachment as slime or the accumulation as sludge could be prevented even when the turbidity of the circulating water was relatively great and the suspended substances were present in the circulating water in a relatively great amount.

In Comparative Example 2 in which part A was added in an amount such that the concentration of effective chlorine was 5 mg/liter without adding part B, the fraction of preventing attachment of slime and the fraction of preventing accumulation of sludge were both about 60%. Even when the amount of part A was increased to 10 mg/liter in Comparative Example 3, the fraction of preventing attachment of slime and the fraction of preventing accumulation of sludge were both about 80%. Thus, it is shown that the combined use of part A and part B in Examples 1 to 6 exhibited the synergistic effect. In Comparative Examples 2 and 3, the smaller turbidity of the circulating water than that in Examples 1 to 6 show that the amount of the suspended substances remaining in the water was smaller and the amount of the suspended substances which was flocculated and attached as slime and accumulated as sludge was greater.

In Comparative Examples 4 to 13 in which part B comprising the anionic polymer or the phosphonic acid alone was added in an amount such that the concentration of solid components was 5 mg/liter or 10 mg/liter without adding part A, the fraction of preventing attachment of slime and the fraction of preventing accumulation of sludge were both small. Thus, it is shown that the combined use of part A and part B in Examples 1 to 6 exhibited the synergistic effect. In Comparative Examples 4 to 13, the effect of preventing accumulation of sludge is poorer than the effect of preventing attachment of slime. In Comparative Examples 4 to 13, the turbidity of the circulating water was smaller than that in Examples 1 to 6 and Comparative Examples 2 and 3 and it is shown that the amount of suspended substances remaining in the water was smaller.

As shown in Table 2, the number of microorganisms in the circulating water in Comparative Example 1 was not substantially different from those in circulating water in Comparative Examples 2, 4 and 8 and it is shown that the microbicidal effect is not exhibited when part A alone was added in an amount such that the concentration of effective chlorine was 5 mg/liter or part B alone was added in an amount such that the concentration of solid components was 5 mg/liter. The fact that, in accordance with the present invention, the excellent effects of preventing attachment of slime and accumulation of sludge were exhibited at a small concentration such that the effective microbicidal effect could not be obtained in accordance with conventional technology shows that the formation of viscous substances by microorganisms and bioflocculation by the modifying activity could be prevented even when the microbicidal effect was not exhibited. It is also considered that the synergistic effect could be obtained by the dispersion effect and the combined use of the component having the sealing property.

Example 7

A composition composed of 40% by weight of an aqueous solution of sodium hypochlorite having a concentration of effective chlorine of 12% by weight, 8% by weight of sulfamic acid, 10% by weight of an anionic polymer or a phosphonic acid and the remaining amount of sodium hydroxide and water was prepared. pH of the composition was adjusted by changing the amount of sodium hydroxide. The prepared composition was stored in a vessel kept at the constant temperature of 40° C. and shielded from light. The concentration of the effective chlorine was measured after the composition was stored for a prescribed time.

For the measurement of the concentration of the effective chlorine, a residual chlorine meter manufactured by HACH Company and a reagent specific for this measurement were used. BELCREN (the weight-average molecular weight: 2730) manufactured by GREAT LAKES CHEMICAL Company was used as the polymaleic acid. ISOBAN (the weight-average molecular weight: 10,800) manufactured by KURARAY Co., Ltd. was used as the maleic acid-isobutylene copolymer. AQUARICK GL (the weight-average molecular weight: 10,700) manufactured by NIPPON SHOKUBAI Co., Ltd. was used as the acrylic acid-hydroxyallyloxypropanesulfonic acid copolymer. DEQUEST 2010 manufactured by MONSANTO Company was used as 1-hydroxyethylidene-1,1-diphosphonic acid. BAYHIBIT AM manufactured by BAYER Company was used as 2-phosphonobutane-1,2,4-tricarboxylic acid. BELCORE 575 manufactured by GREAT LAKES Company was used as hydroxyphosphonoacetic acid.

The results are shown in Table 4. In the aqueous solution of sodium hypochlorite, the concentration of effective chlorine remained only by about 60% after one month and about 20% after 3 month at pH 14. In contrast, the compositions prepared above showed excellent stability when pH had great values. It was confirmed that the effective chlorine remained after 3 months by as much as 50% or more at pH 12 and 90% or more at pH 13 or greater. It was also confirmed that the compositions were very unstable at pH 11. As shown above, the stability of the agent comprising the chlorine-based microbicidal agent, sulfamic acid compound or a salt thereof and a compound selected from an anionic polymer, a phosphonic acid and a salt of a phosphonic acid depends on pH and very excellent stability can be obtained at pH 12 or greater.

TABLE 4

| Composition | pH of composition | Fraction of remaining effective chlorine (%) | | |
| --- | --- | --- | --- | --- |
| | | after 7 days | after 30 days | after 90 days |
| Aqueous solution of sodium hypochlorite alone | 14 | 91 | 59 | 18 |
| Sodium hypochlorite + sulfamic acid + sodium hydroxide | 14 | 100 | 100 | 99 |
| | 13 | 100 | 100 | 99 |
| | 12 | 99 | 97 | 89 |
| | 11 | 90 | 63 | 25 |
| Sodium hypochlorite + sulfamic acid + sodium hydroxide + polymaleic acid | 14 | 100 | 99 | 98 |
| | 13 | 97 | 97 | 94 |
| | 12 | 96 | 91 | 75 |
| | 11 | 76 | 33 | 5 |
| Sodium hypochlorite + sulfamic acid + sodium hydroxide + maleic acid-isobutylene copolymer | 14 | 100 | 99 | 99 |
| | 13 | 100 | 99 | 98 |
| | 12 | 99 | 95 | 86 |
| | 11 | 83 | 45 | 8 |
| Sodium hypochlorite + sulfamic acid + sodium hydroxide + acrylic acid-hydroxyallyloxypropanesulfonic acid copolymer | 14 | 98 | 99 | 96 |
| | 13 | 98 | 94 | 90 |
| | 12 | 86 | 50 | 15 |
| | 11 | 51 | 4 | 1 |
| Sodium hypochlorite + sulfamic acid + sodium hydroxide + 1-hydroxyethylidene-1,1-diphosphonic acid | 14 | 100 | 95 | 90 |
| | 13 | 98 | 83 | 61 |
| | 12 | 90 | 78 | 50 |
| | 11 | 55 | 8 | 0 |
| Sodium hypochlorite + sulfamic acid + sodium hydroxide + 2-phosponobutane-1,2,4-tricarboxylic acid | 14 | 100 | 100 | 99 |
| | 13 | 100 | 100 | 99 |
| | 12 | 99 | 96 | 87 |
| | 11 | 85 | 45 | 8 |

TABLE 4-continued

| Composition | pH of composition | Fraction of remaining effective chlorine (%) | | |
|---|---|---|---|---|
| | | after 7 days | after 30 days | after 90 days |
| Sodium hypochlorite + sulfamic acid + | 14 | 100 | 100 | 99 |
| sodium hydroxide + hydroxyphosphonoacetic acid | 13 | 99 | 99 | 97 |
| | 12 | 99 | 94 | 83 |
| | 11 | 62 | 10 | 2 |

INDUSTRIAL APPLICABILITY

In accordance with the composition and the process for preventing formation of slime of the present invention, attachment of slime to pipings, heat exchangers and various instruments can be prevented and accumulation of sludge in water tanks and separating plates in heat exchangers can also be effectively prevented by adding the composition in a small amount such that no microbicidal effects are exhibited. As the result, it is made possible that troubles caused by attachment of slime and accumulation of sludge in various water systems are prevented and the cost required for cleaning can be remarkably decreased.

The invention claimed is:

1. A composition for preventing formation of slime which consists essentially of sodium hypochlorite having a concentration of effective chlorine of 1 to 8% by weight, 1.5 to 9% by weight of sulfamic acid and at least one anionic polymer having a solid concentration of 0.5 to 4% by weight, said anionic polymer being selected from the group consisting of polymaleic acid, polyacrylic acid, a copolymer of acrylic acid and 2-hydroxy-3-allyloxypropane sulfonic acid, a copolymer of acrylic acid and 2-acrylamide-2-methylpropane sulfonic acid a copolymer of acrylic acid and isoprene sulfonic acid, a copolymer of acrylic acid and 2-hydroxyethyl methacrylate, a copolymer of acrylic acid, 2-hydroxyethyl methacrylate and isopropylene sulfonic acid, a copolymer of maleic acid and pentene, a copolymer of maleic acid and isobutylene, an alkaline metal salt of said anionic polymer and an alkaline earth metal salt of said anionic polymer wherein said anionic polymer has a weight-average molecular weight in the range of 500 to 50,000, and 2.5 to 20% by weight of sodium hydroxide, each of said concentrations expressed in a percentage being calculated on the total amount by weight of the composition, and said composition has a pH of 12 or greater.

2. The composition according to claim 1, wherein the anionic polymer is a copolymer of maleic acid and isobutylene.

3. The composition according to claim 1, wherein the anionic polymer is polymaleic acid.

4. The composition according to claim 1, wherein the anionic polymer is polyacrylic acid.

5. The composition according to claim 1, wherein the anionic polymer is at least one polymer selected from the group consisting of a polymaleic acid, polyacrylic acid and a copolymer of maleic acid and isobutylene.

6. A composition for preventing formation of slime which consists essentially of:
  a component A which has a pH of 12 or greater, said component A consists essentially of (a) sodium hypochlorite having a concentration of effective chlorine of 1 to 8% by weight, (b) 1.5 to 9% by weight of sulfamic acid, and (c) 2.5 to 20% by weight of sodium hydroxide, each of said concentrations expressed in a percentage being calculated based on the total amount by weight of said component A; and
  a component B, which consists essentially of (d) at least one anionic polymer, the solid concentration of which is 10 to 60% by weight of the total amount of said component B, wherein said anionic polymer is selected from the group consisting of polymaleic acid, polyacrylic acid, a copolymer of acrylic acid and 2-hydroxy-3-allyloxypropane sulfonic acid, a copolymer of acrylic acid and 2-acrylamide-2-methylpropane sulfonic acid, a copolymer of acrylic acid and isoprene sulfonic acid, a copolymer of acrylic acid and 2-hydroxyethyl methacrylate, a copolymer of acrylic acid, 2-hydroxyethyl methacrylate and isopropylene sulfonic acid, a copolymer of maleic acid and pentene, a copolymer of maleic acid and isobutylene, an alkaline metal salt of said anionic polymer and an alkaline earth metal salt of said anionic polymer, wherein said anionic polymer has a weight-average molecular weight in the range of 500 to 50,000.

7. The composition according to claim 4, wherein the anionic polymer is a copolymer of maleic acid and isobutylene.

8. The composition according to claim 4, wherein the anionic polymer is polymaleic acid.

9. The composition according to claim 4, wherein the anionic polymer is polyacrylic acid.

10. A process for preventing formation of slime in a water system comprising adding a composition for preventing formation of slime to said water system, the composition consisting essentially of sodium hypochlorite having a concentration of effective chlorine of 1 to 8% by weight, 1.5 to 9% by weight of sulfamic acid and at least one anionic polymer having a solid concentration of 0.5 to 4% by weight, said anionic polymer being selected from the group consisting of polymaleic acid, polyacrylic acid, a copolymer of acrylic acid and 2-hydroxy-3-allyloxypropane sulfonic acid, a copolymer of acrylic acid and 2-acrylamide-2-methylpropane sulfonic acid, a copolymer of acrylic acid and isoprene sulfonic acid, a copolymer of acrylic acid and 2-hydroxyethyl methacrylate, a copolymer of acrylic acids 2-hydroxyethyl methacrylate and isopropylene sulfonic acid, a copolymer of maleic acid and pentene, a copolymer of maleic acid and isobutylene, an alkaline metal salt of said anionic polymer and an alkaline earth metal salt of said anionic polymer wherein said anionic polymer has a weight-average molecular weight in the range of 500 to 50,000, and 2.5 to 20% by weight of sodium hydroxide, each of said concentrations expressed in a percentage being calculated based on the total amount by weight of the composition, and said composition has a pH of 12 or greater.

11. A process for preventing formation of slime according to claim 10, wherein the water system is a cooling water system, a heat-storage water system, a water system for manufacturing paper and pulp, a water system for collecting dusts or a scrubber water system.

12. A process for preventing formation of slime comprising adding a composition for preventing formation of slime to a water system, the composition consisting essentially of:
- a component A, which has a pH of 12 or greater, said component A consisting essentially of (a) sodium hypochlorite having a concentration of effective chlorine of 1 to 8% by weight, (b) 1.5 to 9% by weight of sulfamic acid, and (c) 2.5 to 20% by weight of sodium hydroxide, each of said concentrations expressed in a percentage being calculated based on the total amount by weight of said component A; and
- a component B, which consists essentially of (d) at least one anionic polymer, the solid concentration of which is 10 to 60% by weight of the total amount of said component B, wherein said anionic polymer is selected from the group consisting of polymaleic acid, polyacrylic acid, a copolymer of acrylic acid and 2-hydroxy-3-allyloxypropane sulfonic acid, a copolymer of acrylic acid and 2-acrylamide-2-methylpropane sulfonic acid, a copolymer of acrylic acid and isoprene sulfonic acid, a copolymer of acrylic acid and 2-hydroxyethyl methacrylate, a copolymer of acrylic acid, 2-hydroxyethyl methacrylate and isopropylene sulfonic acid, a copolymer of maleic acid and pentene, a copolymer of maleic acid and isobutylene, an alkaline metal salt of said anionic polymer and an alkaline earth metal salt of said anionic polymer wherein said anionic polymer has a weight-average molecular weight in the range of 500 to 50,000.

* * * * *